United States Patent [19]

Schmitt et al.

[11] Patent Number: 4,888,818

[45] Date of Patent: Dec. 19, 1989

[54] METHOD AND APPARATUS FOR THE DETERMINATION OF THE SETTING PROCESS IN AN INORGANIC AQUEOUS BINDER SYSTEM

[75] Inventors: Wolfgang Schmitt, Neu Isenburg; Dietmar Bege, Erlangen, both of Fed. Rep. of Germany

[73] Assignee: Siemens Aktiengesellschaft, Munich, Fed. Rep. of Germany

[21] Appl. No.: 43,835

[22] Filed: Apr. 28, 1987

[30] Foreign Application Priority Data

Apr. 29, 1986 [DE] Fed. Rep. of Germany ....... 3614468

[51] Int. Cl.$^4$ ...................... G01N 27/02; G01R 27/02
[52] U.S. Cl. ..................................... 324/439; 324/441; 324/65 R; 374/53
[58] Field of Search ...................... 324/65 R, 439, 441, 324/444; 73/53, 64.1, 73, 432.1, 866.2; 364/420, 422, 732; 374/53

[56] References Cited

U.S. PATENT DOCUMENTS

| | | | |
|---|---|---|---|
| 3,791,792 | 2/1974 | Lindsay | 374/53 X |
| 3,965,414 | 6/1976 | Teass, Jr. | 324/441 |
| 4,120,166 | 10/1978 | Brooks | 405/225 |
| 4,524,319 | 6/1985 | Eberling et al. | 324/65 R |
| 4,566,806 | 1/1986 | DeBondt | 374/53 |

FOREIGN PATENT DOCUMENTS 430768 6/1926 Fed. Rep. of Germany .

OTHER PUBLICATIONS

Nishimura, Patents Abstracts of Japan, vol. 6, No. 18, Feb. 2, 1982.

Primary Examiner—Reinhard J. Eisenzopf
Assistant Examiner—Jack B. Harvey
Attorney, Agent, or Firm—Herbert L. Lerner; Laurence A. Greenberg

[57] ABSTRACT

A method for the determination of the setting process in an inorganic aqueous binder system, in that the electrical conductivity is constantly measured in the binder system, in that the variation of the electrical conductivity is differentiated according to time, in that the variation of the first derivative of the conductivity is monitored, and in that the temperature in the binder system is continously measured and the temperature dependence of the electrical conductivity is eliminated by means of the measured temperature values.

4 Claims, 1 Drawing Sheet

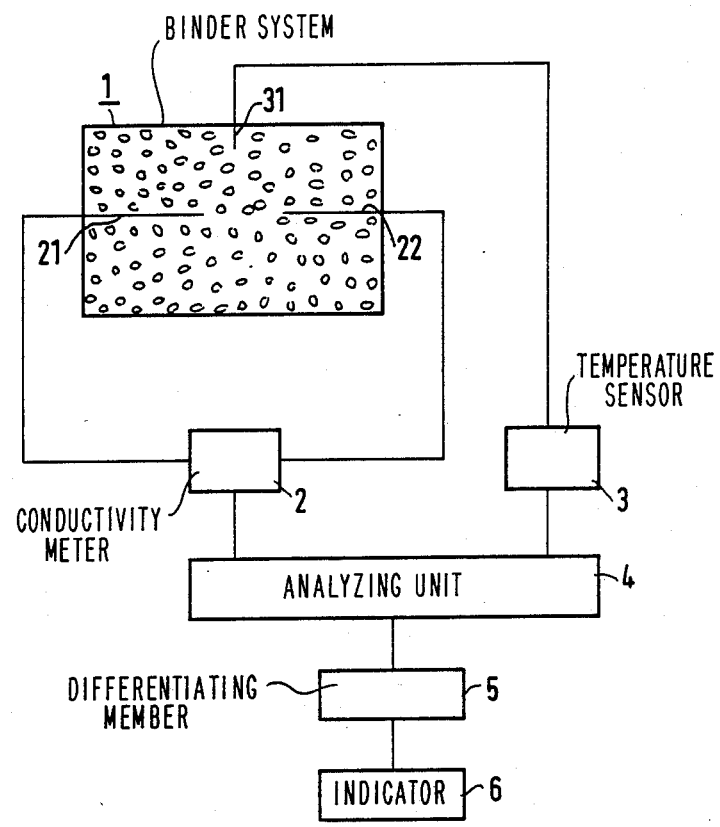

METHOD AND APPARATUS FOR THE DETERMINATION OF THE SETTING PROCESS IN AN INORGANIC AQUEOUS BINDER SYSTEM

BACKGROUND OF THE INVENTION

1. Field of the Invention

The invention relates to a method for determining the setting process in an inorganic aqueous binder system.

2. Description of the Prior Art

Such a binding material system consists of an inorganic binder and water or an aqueous saline solution. Cement is a suitable inorganic binder. A mixture of binder and water is at first castable and sets by means of a chemical reaction.

Binder systems of cement and water are used to set waste, especially radioactively contaminated waste, in concrete. The setting process is determined by measuring tests.

In chemistry related to concrete, tests of the behavior of concrete during setting are also conducted.

Known methods to determine the setting process are the needle penetration method and the calorimetric method. In the needle penetration method the penetration depth of a weighted needle into the binder system is determined. Reduction of the penetration depth indicates the setting process.

In the calorimetric method, the temperature variation of a thermally insulated probe is registered. Since heat energy is released during setting, a rise in temperature indicates the setting process.

With the known methods it is often impossible to determine the setting process, especially during slow progress of the chemical reaction in the binder system. In a reaction taking several days the temperature rise is so small that the calorimetric method fails. The needle penetration method only gives indications of the setting process in the surface layers. Insights into the setting process in the inside of a body are impossible with this method.

SUMMARY OF THE INVENTION

It is an object of the invention to provide a method for the determination of the setting process in an inorganic aqueous binder system which determines the chemical reaction of the setting.

With the foregoing and other objects in view, there is provided in accordance with the invention a method for the determination of the setting process in an inorganic aqueous binder system, which comprises, continuously measuring the electrical conductivity in an inorganic aqueous binder system to obtain a chronological variation of the conductivity in the binder system, differentiating according to time said chronological variation of the conductivity to form a first derivative according to time to indicate a change of speed of the variation in conductivity, and monitoring the first derivative of the conductivity to determine progress in the setting process of the binder system.

In accordance with the invention, there is provided an apparatus for the determination of the setting process in an inorganic aqueous binder system, comprising, an inorganic binder system to be monitored, a conductivity meter connected with the binder system for continuously measuring the electrical conductivity in the binder system and producing an output signal of the measured values, said conductivity meter is connected with a differentiating member in which a first derivative of the variation of conductivity according to time is formed from the output of the conductivity meter and the member produces an output signal of the first derivative, and an indicator connected to the differentiating member to receive the output signal of the first derivative for recording the differentiated conductivity variation in the binder system.

Other features which are considered as characteristic for the invention are set forth the the appended claims.

Although the invention is illustrated and described herein as embodied in method and apparatus for the determination of the setting process in an inorganic aqueous binder system, it is nevertheless not intended to be limited to the details shown, since various modifications may be made therein without departing from the spirit of the invention and within the scope and range of equivalents of the claims.

BRIEF DESCRIPTION OF THE DRAWING

The invention, however, together with additional objects and advantages thereof will be best understood from the following description when read in connection with the accompanying drawing which diagrammatically illustrates an apparatus for carrying out the method in accordance with the invention for the determination of the setting process in an inorganic aqueous binder system.

DESCRIPTION OF THE PREFERRED EMBODIMENTS

The invention relates to a method and an apparatus for the determination of the setting process in an inorganic aqueous binder system. The electrical conductivity in the binder system is measured continuously by means of a conductivity meter and simultaneously the temperature by means of a temperature sensor in the binder system. The temperature dependence of the electrical conductivity is eliminated in an analyzing unit. The corrected variation independent of temperature of the electrical conductivity is differentiated in a differentiating member. The variation of the first derivative according to time is monitored. The first derivation permits an exact determination of the setting time. The output of the differentiating member is connected with an indicator.

The determination of the setting process in an inorganic aqueous binder system is attained by the invention by continuously measuring the electrical conductivity in the binder system, then differentiating the progress of the electrical conductivity according to time and by monitoring the progress of the first derivative of the conductivity.

The chemical reaction of setting in the binder system leads to a change in the concentration of conductive solutions. The conductivity in the binder system is therefore correlated with the progress of the chemical reaction. A technically accurate monitoring of the changes in conductivity is achieved by monitoring not the conductivity, but the first derivative of the conductivity according to time, i.e. its changing speed. Even a small but rapid change of the conductivity causes a comparatively large change of its first derivative.

Since changes in temperature influence the conductivity besides the setting process, the temperature, for example, is also continuously monitored in the binder system. The temperature dependency of the electrical conductivity is eliminated with the aid of the temperature values measured. Then the variation independent of the temperature of the electrical conductivity is differentiated according to time.

An advantage is gained with the method of the invention in that exact information about the chemical reaction in the binder system is constantly available. The time of the setting can be exactly determined in accordance with the invention, especially when considering the variation of the temperature.

An apparatus for carrying out the methods comprises a conductivity meter disposed in a binder system the setting progress of which is to be monitored. The conductivity meter may have, for example, two electrodes which are inserted into the binder system. In lieu of that a conductivity measuring cell without electrodes can be used. The output of the conductivity meter is connected to a differentiating member in which the first derivative of the measured conductivity variation according to time is formed. An indicator is switched in series with the differentiating member. It always shows the present differentiated conductivity value.

A temperature sensor, for example, is provided in the binder system to determine the variation of the temperature on the binder system. The conductivity meter and the temperature sensor are connected with an analyzing unit. There the conductivity values are corrected according to their dependence on the temperature. The output of the analyzing unit is connected to the differentiating member. The indicator then always shows the presently corrected and differentiated conductivity value.

This value is a good measurement for the progress of the chemical reaction in the binder system.

By means of the invention the advantage is gained that the chemical process of setting of slowly hardening compositions of inorganic binders and water or aqueous saline solutions can be measured exactly. Thus the time of setting, for example during the setting of radioactively contaminated wastes in concrete, can be exactly determined.

The invention is further described in conjunction with the drawing.

A binder system 1 consists of a mixture of inorganic binders and water. The chemical reaction of this system is monitored to determine the setting time. For this purpose two electrodes 21 and 22 of a conductivity meter 2 known in the art are disposed opposite each other in the binder system 1. The continuous variation of the electrical conductivity in the binder system 1 is determined by means of the conductivity meter 2. Furthermore, a probe 31 of a temperature sensor 3 known in the art disposed in a binder system 1, determines the variation in the temperature in the binder system 1. The conductivity meter 2 and the temperature sensor 3 are connected with an analyzing unit 4. The analyzing unit 4 perhaps is a processor programed with the known reaction of conductivity and temperature. There the simultaneously arriving values for conductivity and temperature are correlated. This results in the chronological variation independent of temperature of the conductivity in the binder system 1. The output of the analyzing unit 4 is connected to a conventional differentiating member 5. There the first derivative according to time is formed for the variation of conductivity. This determines the change of speed of the variation in conductivity. This value makes it possible to exactly determine the point of setting. The output of the differentiating member 5 is connected to an indicator 6.

There is claimed:

1. A method for the determination of the setting process in an inorganic aqueous binder system, which comprises, continuously measuring the electrical conductivity in an inorganic aqueous binder system between two electrodes of a conductivity meter, which are disposed opposite each other in the binder system to obtain a chronological variation of the conductivity in the binder system, differentiating according to time said chronological variation of the conductivity to form a first derivative according to time to indicate a change of speed of the variation in conductivity, and monitoring the first derivative of the conductivity to determine progress in the setting process of the binder system.

2. A method in accordance with claim 1, wherein the temperature in the binder system is continuously measured and the temperature dependence of the electrical conductivity is eliminated by means of the measured temperature values.

3. An apparatus for the determination of the setting process in an inorganic aqueous binder system, comprising, an inorganic binder system to be monitored, a conductivity meter connected with the binder system for continuously measuring the electrical conductivity in the binder system and producing an output signal of the measured values, said conductivity meter comprising two electrodes disposed opposite each other, and said conductivity meter being connected with a differentiating member in which a first derivative of the variation of conductivity according to time is formed from the output of the conductivity meter and the member produces an output signal of the first derivative, and an indicator connected to the differentiating member to receive the output signal of the first derivative for recording the differentiated conductivity variation in the binder system.

4. An apparatus in accordance with claim 3, wherein a temperature sensor is connected with the binder system to be monitored, and the conductivity meter and the temperature sensor are connected with an analyzing unit, in which the conductivity values are corrected with respect to their dependence on the temperature and the corrected conductivity values are produced as an output signal, said analyzing unit having an output connected to the differentiating member for transmitting a signal thereto representing the conductivity variation independent of temperature of the binder system.

* * * * *